(12) United States Patent
Mahrer

(10) Patent No.: US 10,214,712 B2
(45) Date of Patent: Feb. 26, 2019

(54) APPARATUS FOR RECEIVING AND CONDITIONING ORGANIC WASTE BY ANAEROBIC BIOCONVERSION

(71) Applicant: Francois-Regis Mahrer, Puplinge (CH)

(72) Inventor: Francois-Regis Mahrer, Puplinge (CH)

( * ) Notice: Subject to any disclaimer, the term of this patent is extended or adjusted under 35 U.S.C. 154(b) by 655 days.

(21) Appl. No.: 14/418,146

(22) PCT Filed: Jul. 30, 2013

(86) PCT No.: PCT/IB2013/056263
§ 371 (c)(1),
(2) Date: May 4, 2015

(87) PCT Pub. No.: WO2014/020544
PCT Pub. Date: Feb. 6, 2014

(65) Prior Publication Data
US 2015/0307827 A1   Oct. 29, 2015

(30) Foreign Application Priority Data

Jul. 30, 2012 (WO) ................. PCT/IB2012/053890

(51) Int. Cl.
*C12M 3/00* (2006.01)
*C12M 1/107* (2006.01)
(Continued)

(52) U.S. Cl.
CPC ............ *C12M 23/36* (2013.01); *C12M 21/04* (2013.01); *C12M 23/34* (2013.01); *C12M 23/42* (2013.01);
(Continued)

(58) Field of Classification Search
CPC ...... C12M 21/04; C12M 23/34; C12M 23/36; C12M 23/42; C12M 23/44; C12M 23/48;
(Continued)

(56) References Cited

U.S. PATENT DOCUMENTS

| | | | |
|---|---|---|---|
| 2,538,412 A * | 1/1951 | Cecil Lawrence K | ...................... C02F 3/2873 126/360.2 |
| 3,528,889 A * | 9/1970 | Portno Antony David | ................. C12C 11/075 435/301.1 |

(Continued)

FOREIGN PATENT DOCUMENTS

| EP | 0263796 | 4/1988 |
|---|---|---|
| GB | 2162195 | 1/1986 |

(Continued)

OTHER PUBLICATIONS

International Search Report and Written Opinion from PCT/IB2013/056263—11 pages.

*Primary Examiner* — Michael L Hobbs
*Assistant Examiner* — Liban M Hassan

(57) ABSTRACT

An apparatus for receiving and processing organic waste by anaerobic bioconversion comprising a closed tank which is the bioconversion site, provided in the top portion thereof with a gasometric bell for storing and pressurizing the biogas produced, around which the external members of the apparatus are distributed on a pod which also forms the support for a body of the digester. The tank, in a preferred embodiment, comprises a main enclosure which is the bioconversion site, and a secondary central enclosure called the crop, intended to receive and store the organic waste to be processed before the dosing of same into the main enclosure to complete the bioconversion. The crop forms a removable subassembly that can be configured in different ways, with a circulation and distribution block on which it is secured and with a liquid-solid phase separator which is mounted over same. This subassembly engages with a mechanical stirrer for stirring the fermentative medium contained inside the tank, driven by the gasometric bell, which is centered and rotated by a drive device, for example one carried by the arm of a telescopic bracket mounted over same, or by a drive ring.

11 Claims, 8 Drawing Sheets

(51) Int. Cl.
*C12M 1/00* (2006.01)
*C12M 1/36* (2006.01)
*C12M 1/33* (2006.01)
*C12M 1/02* (2006.01)
*C12M 1/06* (2006.01)
*C12M 1/34* (2006.01)

(52) U.S. Cl.
CPC ............ *C12M 23/44* (2013.01); *C12M 23/48* (2013.01); *C12M 27/00* (2013.01); *C12M 27/02* (2013.01); *C12M 41/00* (2013.01); *C12M 41/30* (2013.01); *C12M 41/48* (2013.01); *C12M 45/02* (2013.01); *C12M 45/04* (2013.01); *C12M 45/06* (2013.01); *Y02E 50/343* (2013.01)

(58) Field of Classification Search
CPC ...... C12M 27/00; C12M 27/02; C12M 41/00; C12M 41/30; C12M 41/48; C12M 45/02; C12M 45/04; C12M 45/06

USPC ............ 435/267, 290.2, 290.1, 290.4, 291.6
See application file for complete search history.

(56) References Cited

U.S. PATENT DOCUMENTS

| | | | | |
|---|---|---|---|---|
| 4,349,355 | A | * | 9/1982 | Lingappa ............... C12M 21/04 210/180 |
| 4,888,294 | A | * | 12/1989 | Van Wezel ............. C12M 27/02 435/290.1 |
| 6,059,972 | A | | 5/2000 | Mahrer |
| 6,346,412 | B1 | * | 2/2002 | Stormo ............... B01F 3/04539 210/616 |

FOREIGN PATENT DOCUMENTS

| | | |
|---|---|---|
| WO | 9602469 | 2/1996 |
| WO | 9920573 | 4/1999 |

* cited by examiner

Detail A

Cross-section A-A

Detail B

Cross-section B-B

Cut-away profile view

Plan view

Cross-section B-B

Iso view from above right

Face view

Detail 1

View from above

Detail 2

Spread-apart view along cross-section A-A

Iso view from above right

APPARATUS FOR RECEIVING AND CONDITIONING ORGANIC WASTE BY ANAEROBIC BIOCONVERSION

TECHNICAL DOMAIN

This invention concerns an apparatus for receiving and processing organic waste by anaerobic bioconversion, as well as a process for treating an organic waste flow in this apparatus.

The main application of the invention is the treatment of organic waste from the food professions, like the transformation and non-industrial or industrial distribution of perishable food and in particular catering waste. The invention will be described from the latter point of view but the technology is multi-product and other applications are also possible.

BACKGROUND OF THE INVENTION

In the past, alimentary remnants were most naturally used for feeding animals.

Later, in view of their progressive contamination by packing residuals and cleaning chemicals, this traditional form of recycling was replaced by landfill practices or destruction by incineration which are far more expensive and which one currently tries to leave aside, because of their too negative environmental and energetic impact.

Moreover, the disturbances historically generated by landfills and the industrial nature of incineration plants have led to placing them far away from the urban centers, which makes the development of waste collecting networks more and more expensive.

Consequences of this situation are a tendency to longer intermediate storage of alimentary waste with fewer collections, at the price of higher sanitary risks. It is also possible, under the increasing economical pressure of the cost of collection, that a likewise increasing fraction of urban alimentary waste finishes in the sewerages through the toilets.

The answers envisaged up to now for containing the sanitary risk created by alimentary waste between collections are refrigeration or partial sterilization with chemicals; i.e. the expensive and temporary slowdown of the uncontrolled biological activity in dustbins, to be able to preserve the waste without too much nuisance between collection rounds.

Thus there is not currently on the market any proximity solution for biologic treatment and energy recovery at the source of putrescible waste of the food professions, which proposes only palliatives for differing the nuisance by rejecting them farther away.

DISCLOSURE OF THE INVENTION

This invention thus constitutes an alternative to the present practice of mixing all the waste, by subtracting at the source its not yet contaminated organic fraction and its local and immediate treatment in a specially designed digester.

A digester which does not resemble such installations as exist in for example the countryside of India or of China, but for the first time constitutes a machine which is mass produced, delivered, installed, connected and started like other professional facilities has been described and claimed as a first vision of such product in U.S. Pat. No. 6,059,972, as well as in WO96/02469.

Contrary to the latter, this invention offers a functional approach and an entirely reconsidered constructive conception as to efficiency, cost, integration and maintenance of the technology, in order to satisfy the most exacting conditions, starting with those of catering. Furthermore, the new realisation presents a greatly improved energy balance, which results from the simplification and relocation of its elements, in particular those of motorization which now work in the insulated enclosure of the digester, at the thermostat-controlled temperature of the latter, as well as from the introduction of a heat recovery device on the effluent in order to preheat the incoming materials.

After hygiene, the second constraint found in catering institutions is the narrowness of the work spaces, or even their localization in comparison with the space reserved for customers.

The characteristics of the present invention fully meet these problems:

A first characteristic of the invention is the definition given to the waste treatment device, the dimensional and ergonomic qualities of which allow its integration in work surfaces of kitchens of small institutions and in offices for the larger ones.

In a first case, the digester is linked to the grinder by a unique waste transport piping and, in a second case, by a double piping connected to the classic and often pre-existing systems for grinding and transporting the waste in liquid suspension by means of a partially closed circuit.

A second characteristic of the invention is that the digester can be simultaneously connected to one or more waste production stations and has the capacity of managing them in parallel.

A third characteristic of the invention is that the digester can be situated several dozens of meters away from the grinders, in or outside buildings, on the ground or underground in a suitable chamber, for example under parking places in saturated urban environments.

A fourth characteristic of the invention is the conception of the machine and its peripherals according to their maintenance, which allows all useful operations to be carried out in minimal time, without risk for the active biology and without perturbation for the user, even in the middle of activities.

Finally, the sum of the solutions provided by the invention makes it a real alternative to the system of organic waste dustbins with its numerous economic and sanitary drawbacks, while occupying less space on the workplace.

Other aspects of the invention are set out in the claims.

The invention thus proposes an apparatus for receiving organic waste and treating it by anaerobic bioconversion including a closed tank which is the bioconversion site, equipped in its upper part with a gasometric dome for storing and pressurizing the biogas produced, around which the external elements of the apparatus are distributed on a carrier which also constitutes the support of bodywork of the apparatus;

According to the invention the tank forms a main enclosure containing an internal and central secondary enclosure called gizzard, the internal setup and connections of which can be adapted to the digestion conditions (several ways of digestion, in particular infinitely mixed single-phase and diphasic with fixed biomass), the apparatus being configured to operate in two operating modes:

in the first mode, the level in the main enclosure is stable and that in the gizzard is variable for receiving and storing the substrate prepared with the organic waste to be treated, before dosing it into the main enclosure to feed the bioconversion;

in the second mode, the level in the main enclosure varies according to its supply with substrate and the level in the gizzard which is stabilized by elements for support and concentration of the active biomass housed in it.

In a first case, the gizzard forms a subassembly with a circulation and distribution block on which it is fixed and with a liquid/solid phase separator which surmounts it, and said subassembly at the same time constitutes the support and the rotating bearing for a mechanical stirrer of the fermentative environment contained in the main compartment of the tank, driven by the gasometric dome, which is centred and driven in rotation by a motorization device carried either by an arm of a telescopic bracket which surmounts it, or by a driving crown.

In a second case, the gizzard is linked with a circulation and distribution unit which is outside the tank, carried by the carrier, which also constitutes the support and the rotating shaft of the mechanical stirrer with a liquid/solid phase separator which surmounts it.

Preferably, the gasometric dome has two concentric compartments separated by an annular wall, the outside compartment surmounting the main compartment of the tank and the central one surmounting the gizzard, in such a way that, when a depressurization of the apparatus is created, the gasometric dome fits on a gasket arranged on the circumference of the phase separator which surmounts the gizzard and insulates them fluidtightly from the main enclosure of the tank.

In this embodiment, the upper part of the central compartment of the gasometric dome is formed by a gate the opening of which, after disconnection of the driving system, when it is carried by the arm of the bracket and rotation of the latter, gives access to the internal elements of the gizzard with neither breaking the containment of the main enclosure of the tank nor perturbing the anaerobic biological process taking place in the main enclosure.

According to this embodiment, the upper part of the peripheral compartment of the gasometric dome includes, on both sides of its wall, a double set of sheaths arranged symmetrically and constituting respectively the female parts of a jaw clutch driving the dome by the mobile equipment of the bracket arm on one side and, on the other side, the female part of the drive for the stirrer of the digestion compartment.

The application point of the driving arm for rotating the dome and those of the stirrer driven by the latter are, for example, located at the same height, in order to allow the vertical clearance of the gasometric dome without creating a parasitic torque which would tend to restrict its free play.

The telescopic bracket can be arranged for allowing the total extraction of the gasometric dome from its hydraulic joint, its rotation and its removal, thus allowing access to the totality of the internal elements of the tank.

Generally, in a first case the distribution and circulation block has a compartmentalized housing connected to the circuits of the circulating substrate, in which a volumetric pump is housed as well as a multiway distributor, for example a four-way and four-position one, itself controlled by an indexer that can be inside or outside the distribution and circulation block, as well as the tank itself; and in a second case, the distribution and circulation block is arranged on the holder part of the apparatus which surmounts the tank and is connected to the gizzard by the hollow bodies forming its cradle, and/or by pipes passing inside the hollow bodies.

Said multiway distributor can have a core in the form of a removable cartridge comprising a rotating recipient that can be spherical, as regards its useful seats, bearings and gaskets, in order to be able to be put into position and fit together simultaneously by simple plugging into its housing.

The multiway distributor has four positions:
in a first position (P1) the distributor directly establishes the transfer circuit of the substrate from the grinder to the gizzard body, via the pipe;
the second position (P2) of the distributor establishes, via the first chamber of the housing, a circuit for stirring the substrate by recirculation of the latter between the input of the pump situated at the bottom of the gizzard and its free surface;
the third position (P3) of the distributor establishes, via the second chamber of the housing, a circuit between the gizzard body and the tank, for its permanent supply and to ensure functions of homogenization and/or of thickening of the substrate by overflowing from one compartment into the other, with or without activation of the phase separator;
the fourth position (P4) of the distributor directly establishes a transfer circuit of the substrate between the gizzard body and the outside of the apparatus, by the pipe.

In this embodiment, the housing is compartmentalized by two concentric partitions defining with the former three chambers, connecting respectively:
a) the gizzard body with itself in order to allow its stirring by recirculation of the substrate,
b) the gizzard body with the tank for its supply, and
c) the phase separator with the outlet of the separated liquid fractions.

The third chamber of the housing constitutes a section of the gravity discharge circuit of the liquid fractions leaving the phase separator.

The gizzard is preferably composed of a central body of cylindrical form with double walls, surmounted by a removable phase separator equipped with hydrasive grates interchangeable through the gate of the gasometric dome.

Channels provided in the double wall of the gizzard body allow respectively gravity discharge of the supernatant liquid filtered by the phase separator which surmounts it and, in the opposite direction, recirculation of the contents of the gizzard within itself in closed circuit, via openings in the upper part of its internal wall, immediately under the separator.

Said gizzard body is connected and fixed removably on the housing of the distribution and circulation unit which serves as its seat and cooperates with the latter to house and fix the pump as well as its distribution peripherals.

The bottom of the gizzard body can be formed by the fastening flange of the central pump and its supply inlets, and is interchangeable or accessible like its distribution peripherals, from the gate of the gasometric dome.

In this case, the gizzard body constitutes the essence or the totality of the bearing of the mechanical stirrer of the digestion compartment, rotated by the gasometric dome.

Still according to this embodiment, the phase separator is fixed removably on the upper part of the body of the phase separator, the crown of which at the same time constitutes the overflow of the fermentative environment on its hydrasive grate and the seat on which the circumference of the central compartment of the gasometric dome comes to rest in order to temporarily withdraw the contents of the gizzard from digestion conditions.

Moreover, said separator cooperates with the body of the gizzard to house and bolt the mechanical stirrer of the digestion compartment in its service position.

Said separator cooperates in the same way with the body of the gizzard to house and lock an also removable optional subassembly composed of a mechanical stirrer and of a fixed biomass zone, encapsulated in one or more filtering device(s).

Finally, the couple formed by the stirrer and the fixed biomass zone constitutes a subassembly which can at any time replace a simple stirrer and this couple constitutes an evolutionary and pre-inoculatable member of the digestion zone that can be introduced there after ventilation of the latter zone and removal of the gasometric dome by means of the bracket arm.

When said pump is located in the gizzard subassembly, it can be driven from the outside of the tank by a rotating axle associated with a hydraulic joint carried by the cover of the gate, or from the inside by a motor integrated into the gizzard subassembly.

In a first case, the pump is driven either by a motor carried by the bracket arm or by the intermediary of the crown.

In a second case, the pump, a removable cartridge of the multiway distributor, and its indexer constitute a subassembly which auto-connects and disconnects automatically to its driving power at the moment of positioning from the inside of the gizzard.

An internal stirring device of the gizzard formed by one or more blades is fastened to the second end of the through axle of the pump motor.

In a first variant of the apparatus, the tank consists of only one piece and carries the totality of the external elements of the machine on an annexed holder which occupies the circumference of the hydraulic joint and constitutes with it the head of the apparatus.

In a second variant the tank is provided in two separable parts, wherein the lower part can be fixed in the ground, and the upper part, formed by a cover equipped with the same holder, is detachable.

In a third variant, the part of the apparatus formed by a hydraulic joint of the gasometric dome is removable and constitutes itself the holder which contains the external elements of the apparatus under a bodywork.

The apparatus according to the invention can be connected to one or more peripherals each including a grinder ensuring the same degree of particle reduction for the materials introduced in the gizzard.

According to one embodiment, the motorization source of the elements of the digester is formed by a circuit of oil under pressure generated by a hydraulic group that works thermically isolated from the apparatus, at its operating temperature and contributes in this way to its heating. The elements supplied with this power are respectively: the central pump, the indexer, the gasometric dome, the jack of the telescopic bracket, and a small aggregate for pressurizing the water necessary for the sequential internal self-cleaning of certain places of the apparatus.

The holder, carrier of its external elements and positioned around the upper opening of the tank, can form, with its bodywork elements, a structurally distinct subassembly conceived to be adapted to the different constructive variants of the tank and service conditions. In this case, said bodywork elements coincide with an internal compartment of the elements of the holder, of which they individually constitute access means, including four compartments of which:

the first compartment manages the retention conditions of the biogas produced as well as its treatment up to the consumption counter, and accommodates:
- a buffer container of water, with a centralized device for maintaining the level of the non-return flow device and optionally of the gasometric dome at their target value, as well as those of adjustable trap systems for extracting the liquid effluents coming from the phase separator and optionally from the fixed biomass cartridge;
- useful captors and securities;
- a hydrogen sulphide filter;
- a water separator;
- a ventilation device for the compartment and appropriate security means for the installation conditions of the digester.

The second compartment houses a device for self-consumption of biogas by the digester and/or for its transfer towards an external consumer, comprising:
- a boiler for the consumption of biogas produced by the digester;
- a consumption counter;
- a thermostatic valve or cartridge for regulating the internal temperature of the digester;
- an internal circulator;
- a device for diverting excess heat and/or biogas towards a consumer outside the digester; (valorization)
- a security and alarm device which deviates biogas towards an appropriate safe outlet in case of breakdown of the boiler, mini flare or other; and
- discharge elements for the burnt gas and for ventilation of the compartment, as well as the appropriate security detectors.

The third compartment houses the hydraulic group and the telescopic bracket system, of which all the components for regulating the circulated hydraulic fluid and the captors enable measurement of the reactive forces of the fermentative environment to its imposed movements.

The fourth compartment contains the electric part of the digester in two different boxes:
- a high-current electrical box, which houses the terminal connections of the digester to the electricity network, fuses and start-up relays of the hydraulic group, circulators and other single or three-phase peripherals;
- a low-current electrical box interconnecting a programmable controller to all its measuring, control, and remote transmission peripherals; and
- an operation control interface with alphanumeric display, alarms and computer connection means for maintenance.

Preferably, the first compartment concentrates additionally, all the connections of the digester to its environment, by means of a preinstalled underground technical duct with its base, which furthermore collects and evacuates excess and process run-off water and washing water, resulting from maintenance.

Automatic operation of the apparatus and its peripherals, as well as its remote monitoring, are preferably assured by a programmable controller, directly or by the intermediary of control means for peripherals, for example grinders. Said controller is arranged for ensuring the total accounting of material flow and fluids circulated inside the apparatus or exchanged by the latter with its environment, as well as the surveillance and the regulation of parameters that might interfere with its operation. Moreover, said accounting includes the counting of the water consumption of each of the grinders connected to the digester, in relation with the waste quantities introduced by each grinder, in order to control their dilution rate.

One can control the apparatus by the subjection of the grinder controller to that of the digester for the regulation of functions which could interfere with its operation, for example dilution of the incoming materials.

The apparatus can have a buffer tank for temporarily storing crushed waste quantities that exceed momentarily the capacity of the digester, the level of which is detected by the latter and the contents progressively taken in.

The invention also concerns a process for implementing the apparatus, in said first operation mode, called "completely mixed", where a substrate to be treated is introduced in the gizzard where first it is stirred by recirculation on itself with the pump and/or homogenized by the blade of its mechanical stirrer; then, with the pump running, the distributor positions itself for a supply sequence of the digestion compartment from the gizzard where the dosage is measured for example by the number of pump revolutions, then the distributor repositions itself in the gizzard stirring mode. Then, the supply of the main enclosure raises the level therein and causes overflowing of the substrate over the overflow of the phase separator, which will filter the supernatant liquid fraction and return the not digested materials into the gizzard, where they will mix with the materials during stirring.

When the pump stops, the internal stirring of the gizzard interrupts and instead there is a stirring sequence of the contents of the main enclosure by its stirrer, both for sharing the supply charge in the entire fermentative environment and for homogenizing the contents, followed by a rest period until the following cycle; and from one cycle to the other, hour after hour, the gizzard voids to leave place for new waste coming from the grinder(s) installed at the production stations.

According to the composition of the substrate, more or less frequent purges will be carried out to avoid a sedimentation of heavy residuals at the bottom of the tank and the accumulation of unwanted light matter, which tends to accumulate in the floating materials zone; or if appropriate, their purge will be caused by overflowing floating materials in the gizzard, followed by its emptying by the position P3 of the distributor.

The invention also concerns a process for implementing the apparatus according to said second operation mode, called "with fixed biomass", where a substrate to be treated obtained after crushing, dilution, and possible complementation of the waste is introduced into the main enclosure of the tank where a first biochemical step of hydrolysis takes place with an important liquefaction of the organic material, this first step being accelerated by stirring and by the temperature in the digester as a function of methanogenesis; the liquid phase is then filtered on a hydrasive grate which surmounts the gizzard, while the non-filtered fraction, inert or not yet hydrolyzed, is returned into the main compartment of the tank or extracted from the digester after spinning by a mechanical device. Then, said liquid phase thus obtained constitutes the substrate of the methanogenic biomass that is fixed and concentrated on the fittings contained in the gizzard, which it recovers permanently and through which it is recirculated by an independent circuit, according to different procedures some of which have the function to purge the excess biomass which otherwise would clog the system; and the process is regulated according to the yield of the biomass fixed and concentrated in the gizzard, whose supply is dosed independently from possible variations in the incoming materials.

Other aspects of the invention are set out in the description which follows and in the drawings.

BRIEF DESCRIPTION OF THE DRAWINGS

Hereinafter, are described, by way of example two main embodiments of the digester, connected to two different conditioning elements, some constructive variants, as well as an implementation mode of the process. For this, reference is made to the attached drawings, namely.

DESCRIPTION OF THE INVENTION

The description concerns the main elements of the digester and its main peripheral device for treatment of incoming waste, in two non-exhaustive constructive variants.

The example chosen shows an installation suitable for the requirements of classic catering establishments from a capacity of about hundred meals/day upwards, daily generating about 25 kg of organic waste from the preparation of meals and remnants of the latter. Reduced to liquid suspension to form about 50 liters of substrate, this waste will need a usable tank volume of 500 liters for its treatment in 10 days in a thermophilic digester working in almost continuous regime, of the kind considered here. The volume of such a digester, including a reasonable space for gas, should not exceed twice that of a water heater of the same usable volume and should supply, starting from the biogas produced, up to double the amount of hot water necessary for cleaning the restaurant's crockery.

On this indicative basis of about 10 L of fermenting space per meal, it is clear that the size of a digester for the in situ treatment of restaurant waste intrinsically matches the size of the facilities which characterize these establishments.

The main subassemblies of the digester consist of a tank 1 inside which a gizzard 2 is fixed on a distribution block 3. A gasometric dome 4, cooperating at the same time with the tank and the gizzard, closes the digester tightly while accumulating biogas at its pressure of use.

Figure 1A:
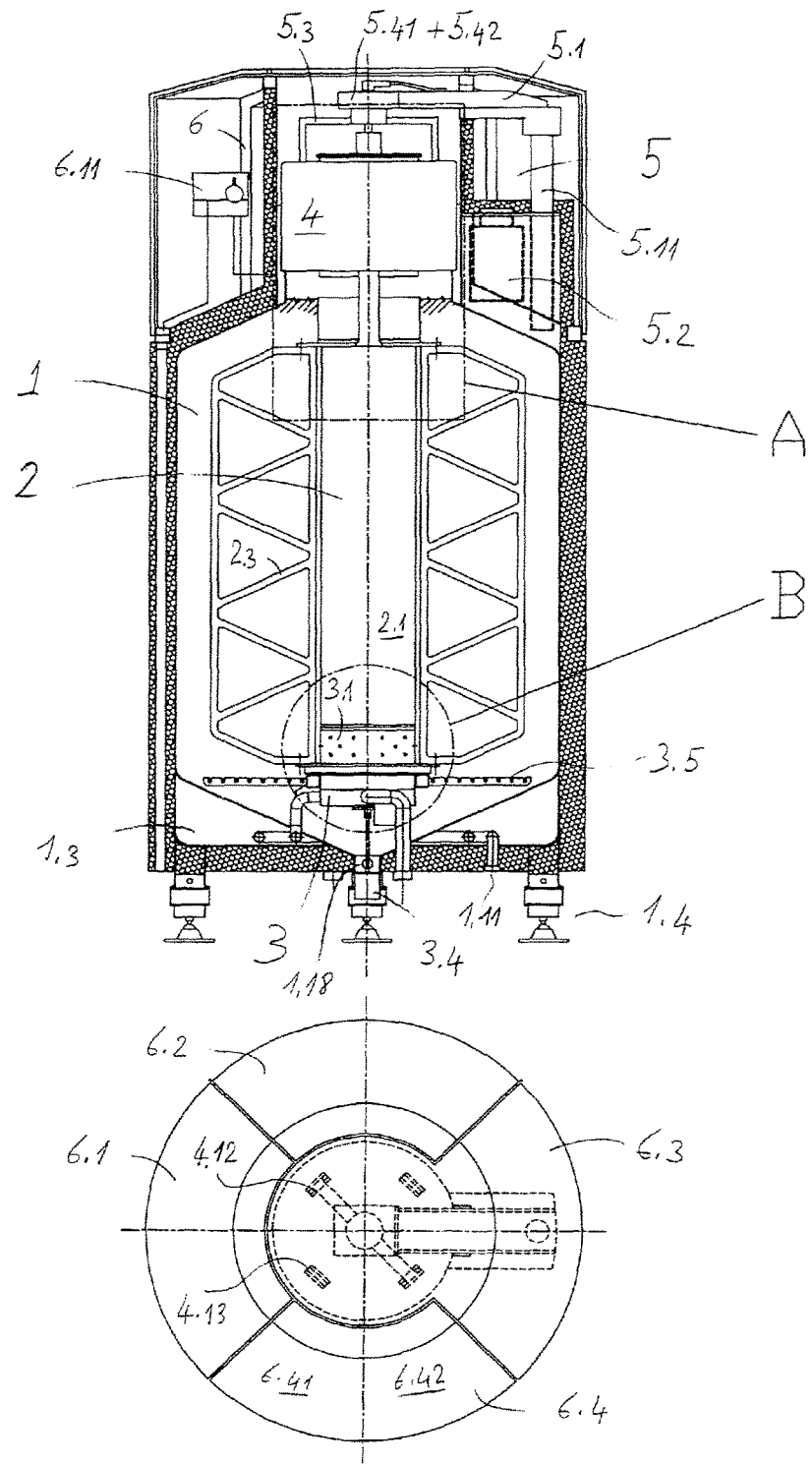
FIG. 1A: schematic view in partial sections of the digester in operation, in a basic design.
Figure 1B:
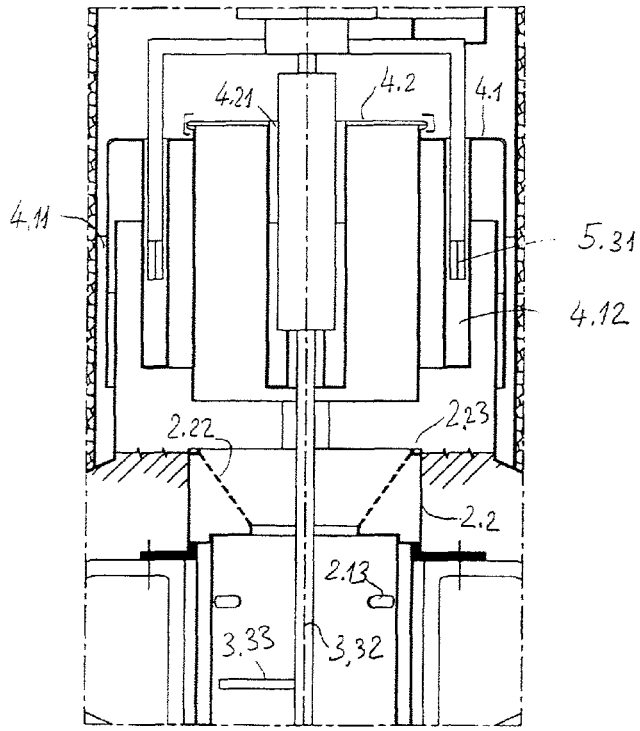
FIG. 1B shows details A and B and sections AA and BB.
Figure 1B:
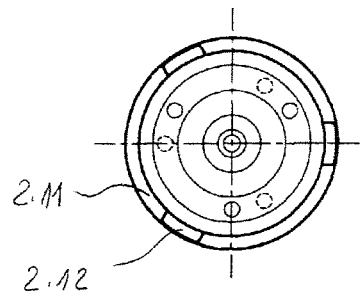
Figure 1B:
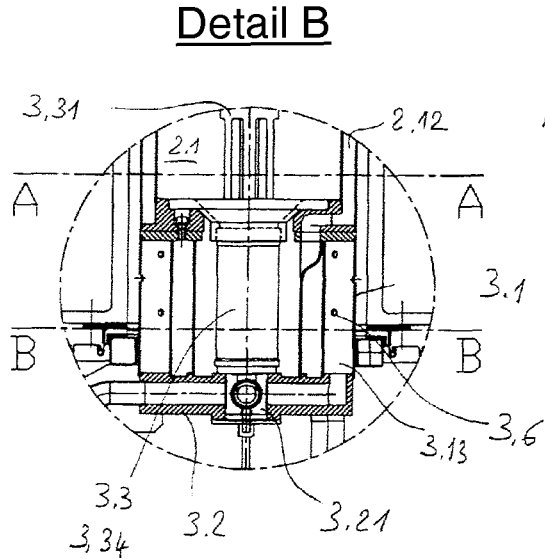
Figure 1B:
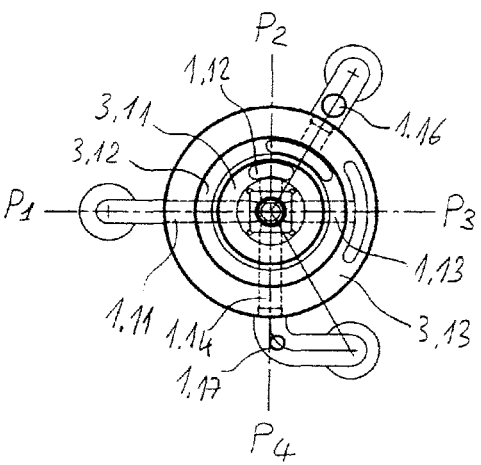
Figure 2:
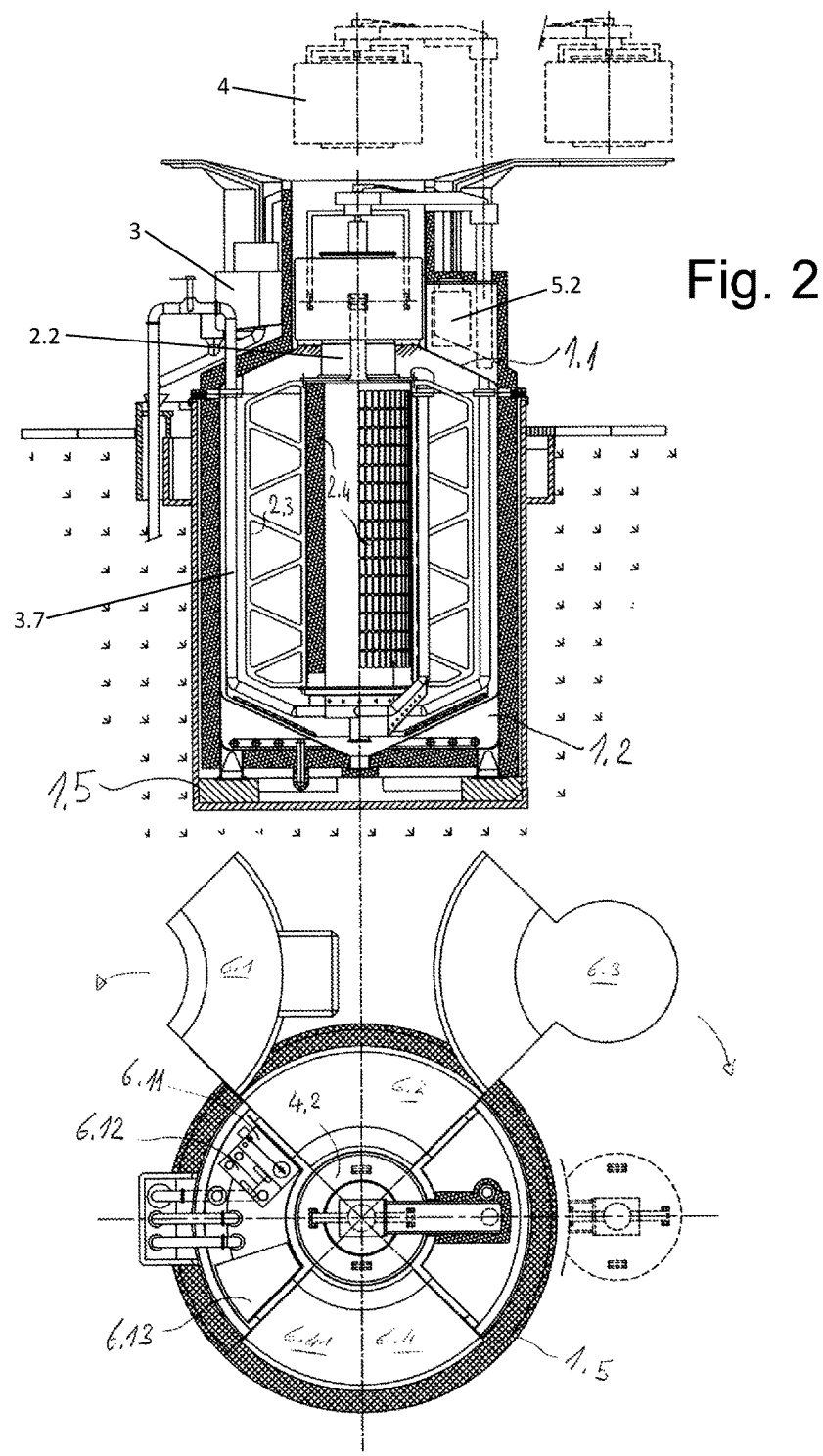
FIG. 2: schematic view in partial section of the digester in maintenance situation, in variant varied embodiment where it is directly fitted in the ground, outside and where it includes an optional zone of fixed biomass.

A pivoting telescopic bracket 5 generates and centres the rotation of the rotating elements of the digester and a holder 6 distributes the external elements of the machine around the gasometric device in compartments which also constitute the bodywork of its upper part (FIG. 1 and FIG. 2).

Figure 3:
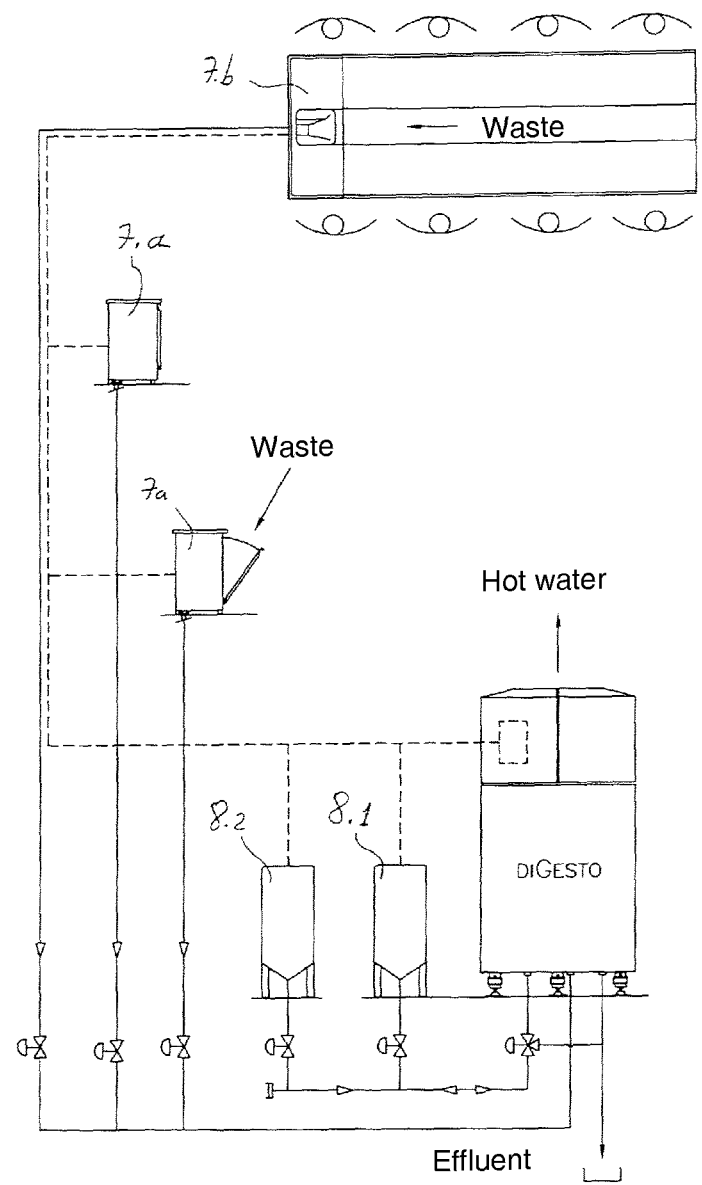
FIG. 3: schematic diagram representing the relationship of the digester with its peripherals.
Figure 4:
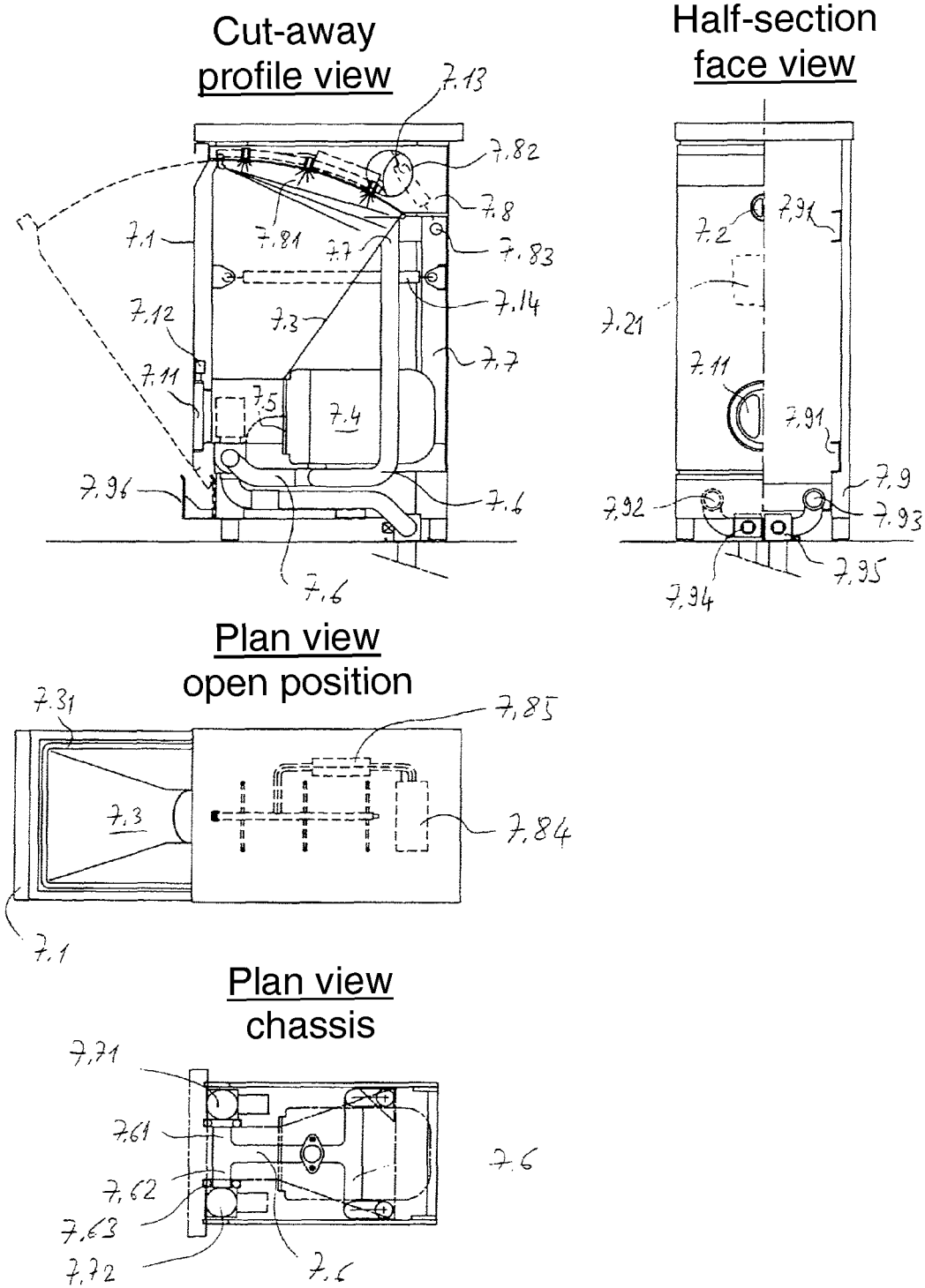
FIG. 4: grinding unit intended for use in a restaurant kitchen.
Figure 5:
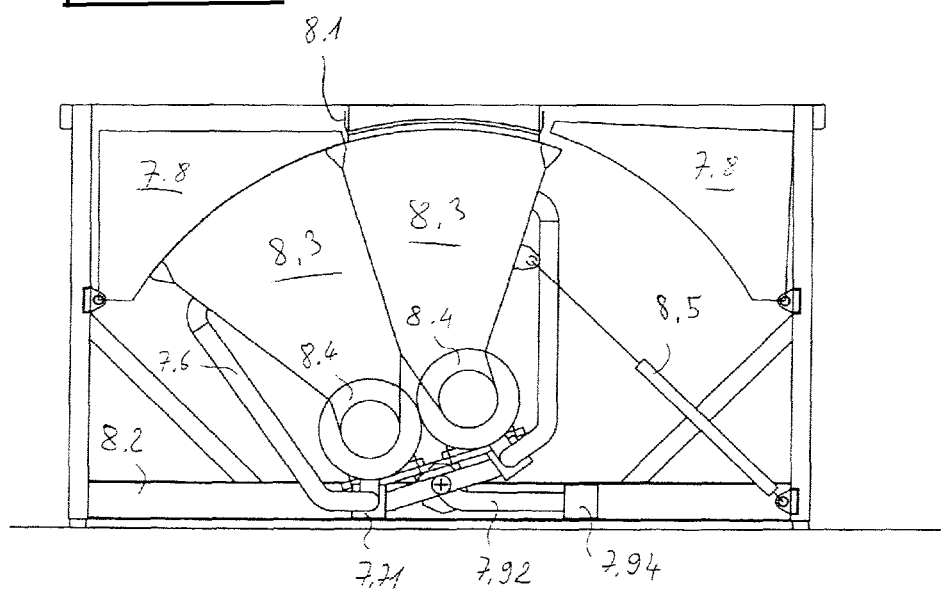
FIG. 5: grinding unit intended for use in an industrial preparation chain.
Figure 5:
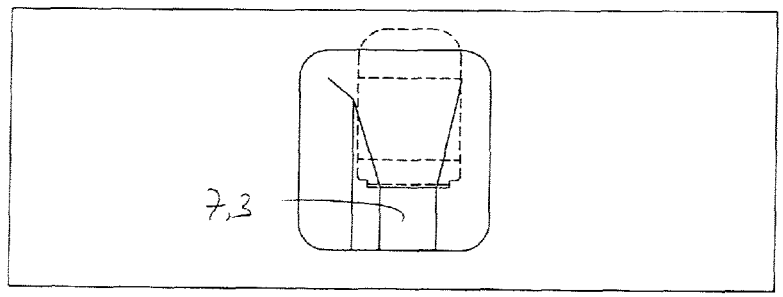

The peripheral subassemblies of the digester are the grinding units 7a and 7b, such as defined for working under the supervision of the controller of the digester and the different retention tanks, 8.1 to 8.n, which can be justified by the nature of the various wastes to be treated, the interest to have co-substrates, etc . . . (FIG. 3, FIG. 4, and FIG. 5).

The tank 1 carries the whole digester. It is heated, thermally" insulated on its whole surface and rests, according to the circumstances, directly on the ground or on a "preinstallation" base, that groups together and rationalizes all its connections in order to facilitate installation, possible exchange, and to avoid thermic bridges.

In the variant of FIG. 1, the tank is connected to the circuits of incoming waste and co-substrates as well as to the discharge ducts by its lower part.

In the variant of FIG. 2, these connections are carried by the upper part of the tank, forming a cover, in order to house its lower part in the ground and/or to make the digester from a greater variety of tanks, as to forms and materials.

To accommodate for all its cases of installation, the tank has a standard base system which is completed by a removable part adapted to its destination (FIG. 1 and FIG. 2).

The gizzard 2 receives the incoming waste and limits the level of substrate in the tank.

Its upper part is formed by a phase separator allowing extraction of the supernatant liquid and return of the not liquefied fraction into the gizzard, by overflowing, with the incoming materials.

Its lower part is formed by the fastening flange of the pump, which includes its supply openings. According to constructive variants, said flange will carry the whole pump or its single lantern (bearing support) when the latter is actuated by an axle, from the outside.

The central part of the gizzard is formed by a double wall inside which channels allow the gravity discharge of the filtered supernatant and, in the other direction, a recycling function of the contents of the gizzard within itself by the pump: FIG. 1, detail A and view A-A.

The gizzard 2 is fixed removably on the distribution and circulation unit, which serves as its seat. FIG. 1, detail B.

The distribution and circulation unit 3 is a fixed or removable subassembly, fastened, according to the considered option, to the base, FIG. 1, or to the part forming a cover of the tank, FIG. 2, by its pipes for connection with the outside.

It is composed of a multiway distributor body surmounted by a compartmentalized housing which allows the circulation of circulated fractions of the substrate and houses the central volumetric pump. Said housing is closed by a connection plate which jointly fixes the volumetric pump and the gizzard. The distribution and circulation unit manages the totality of the substrate flow entering, exiting, and recirculated in the digester.

According to the constructive variants, the pump, the multiway distributor and its actuator constitute a unique removable subassembly which auto-connects automatically at the moment of positioning and conversely. (Not represented)

In the illustrated example, the number of the pipes connected to the body of the distributor is three, one or more with double walls, and the number of paths managed by the distributor is four (FIG. 1, detail B, section B-B).

The gasometric dome 4 has two concentric compartments.

The external compartment is doubly connected to a driving bearing fixed on the bracket arm thereabove and to a mechanical stirrer immersed in the digestion zone, by a device with sliding jaw clutches allowing it to drive the stirrer without obstructing its axial clearance. Its sealing with the tank is assured by a hydraulic joint which protects it against any overpressure or accidental underpressure.

The central compartment of said gasometric dome has the double property to gas-tightly apply on the circumference of the gizzard's opening gizzard when the digester is depressurized, and then allos access to all the internal elements of the gizzard and of the distribution block, by a gate which closes it, whose centre is formed by a second hydraulic joint, ensuring sealing of the passage of the pump's drive shaft, in the variant where the pump is actuated from the outside.

In operation: (FIG. 1, detail A)

The gasometric dome compresses the biogas at its pressure of use, thus allowing gas to be consumed almost in proportion to its production, it drives the mechanical stirrer of the digestion compartment through the zone of the floating materials, preventing the latter from agglomerating to form a crust which could otherwise harden and endanger the digester.

its hydraulic joint(s) protect(s) the bioreactor against any excess pressure or accidental underpressure.

In maintenance: (FIG. 2)

The gasometric dome, after depressurization, rests on the circumference of the phase separator which constitutes the upper part of the gizzard, confining thus the active biomass in the digestion area, comprised between the outer wall of the gizzard and the tank, thus allowing access to the accessible internal elements from the gizzard without disturbing the biological operation of the digester, in case of necessity, its total removal remains possible with the usual precautions, thus allowing access to the totality of the internal elements of the digester.

The pivoting telescopic bracket 5.1 is the support of the whole kinematic linkage of the internal elements of the digester actuated from over it:

the telescopic part is formed by the shaft of a vertical jack operated by a hydraulic aggregation fastened to the upper part of the tank.

the bracket itself is fixed at the end of this shaft and carries driving means for rotating the stirrer of the digestion compartment via the gasometric dome.

In the case where the pump is driven from outside the digester the bracket includes the means for driving the stirrer and the pump axle, in concentric rotations.

In operation:

the bracket positions the driving means of the rotating elements of the digester, at the desired speeds and directions, the bracket takes part in the measurement of the reactive forces opposed by the environment to the movements which it receives from the stirrer immersed in the digestion area and, if applicable, from the central pump.

In maintenance:

the bracket is disconnected from the gasometric dome and, if applicable, from the pump. Once lifted up and pivoted, it allows free access to the central gate of the gasometric dome.

in case of substantial maintenance, the bracket can lift and set down the complete gasometric dome to give free access to all the internal elements of the digester.

the bracket can carry tools for cleaning under pressure, extraction or reassembly of the internal elements of the digester.

The holder 6 is a subassembly that concentrates the external elements of the digester and its connection means to power sources, in all variants.

Placed on top of the digester, the holder is made with pre-equipped compartments associated with covers, to form together a bodywork allowing the digester to function outside and inside, protected against unauthorized interventions.

The setup of these compartments and of their access means depends on the particular installation of the digesters.

Operation

The flows of substrate in the machine are totally managed by the distribution and circulation unit, itself piloted by the programmable controller of the digester, the sequences of the program of which successively control the positioning of the distributor, the start-up in one direction or in the other of the volumetric pump with selected speeds and durations or numbers of revolutions, as well as rest times influenced by various parameters.

DETAILED DESCRIPTION

The tank 1, in all its variants, carries the totality of the elements of the digester and rests, according to the circumstances, directly on the ground or on a pre-installation base that groups together and rationalizes all its connections, in order to facilitate installation, possible exchange and to avoid thermic bridges.

The base can for example have the form of a chamber fixed in and connected to the ground, according to FIG. 2.

To accommodate for all these cases of installation, the tank has a standard base system 1.4, which is completed by a removable part adapted to its destination.

In its variant shown by FIG. 1, the tank 1 is connected to the circuit(s) of incoming waste and outgoing effluents in its lower part, by pipes for connection and fastening to the tank of the circulation block 3 which also constitutes the base of the gizzard. In this embodiment, the tank consists of only one piece and the all its internal elements are introduced through the opening in its upper part, which is closed by the gasometric dome 4.

In its variant shown by FIG. 2, the digester is made of two parts, all its connections being provided at its upper part 1.1, forming a cover, in order to allow, for example, its installation in the ground without need to have access for maintenance and/or to facilitate its production from tanks 1.2 of varied kinds and forms.

In the first case, the tank 1 has a double jacket 1.3 ensuring both its own heating and the reheating of the incoming materials.

In the second case, the reheating of the incoming materials is connected to the part 1.1 forming a cover of said tank.

In all cases, the tank has a conical base, to concentrate sediments in a point where they can be extracted easily, by the emptying opening 1.16, which can possibly have the form of an aspiration cannula put in place from the holder.

In all cases too, be it removable or not, it is the upper part of the tank which carries the external elements of the digester, collected in the holder 6 connected to power, compartmentalized, insulated and encased in order to work outside and indoors.

The gizzard 2 is composed of a central body 2.1 surmounted by a removable phase separator 2.2. It is fixed on the housing 3.1 of the distribution and circulation unit 3 which serves as its seat.

The central body 2.1 of the gizzard is a cylindrical enclosure with double walls, between which channels 2.11 and 2.12 allow respectively the gravity discharge of supernatant liquid filtered by the phase separator 2.2 and, in the opposite direction, to re-pump the contents of the gizzard within itself in closed circuit, by the openings 2.13 in the upper part of its internal wall, immediately under the separator 2.2.

In its upper part, the gizzard houses and fixes the body of the phase separator 2.2, whose crown 2.21 constitutes at the same time the overflow of the fermentative environment on its hydravise grate 2.22, and the seat on which the circumference of the central compartment of the gasometric dome comes to rest, the effect of which is to temporarily subtract the contents of the gizzard to the digestion conditions.

In its lower part, the central body 2.1 of the gizzard connects removably to the housing 3.1 of the distribution and circulation unit 3, in order to connect the respective ducts of the circulating flow between the two elements and to fix the volumetric pump 3.3 whose aperture, or the motor in its housing 3.31, partially constitutes its base.

According to the first considered constructive variant, the gizzard is traversed by the driving axle 3.32 of said pump, which also constitutes the support of several functions and accessories, such as blades 3.33 contributing to the stirring of its contents and nozzles for self-cleaning by projecting hot water or vapor under high pressure.

Driven by an external motorized bearing 5.4 carried by the bracket 5.1, the axle 3.31 passes through the gasometric dome fluidtightly, by means of a hydraulic joint 4.21 localised on the gate 4.2 of its central compartment.

According to the second constructive variant, the pump, the multiway distributor and its actuator constitute a unique removable subassembly which auto-connects automatically at the moment of fitting in place, and conversely. By this conception, the complete revision of all internal distribution and circulation elements for the substrate in the digester is ensured by simply replacing said subassembly, without incidence for the operation of its internal biology.

According to the same variant, the internal stirring device of the gizzard, formed by one or more blades, is fastened, according to a preferred embodiment, to the second end of the axle of the pump's hydraulic motor, and the self-cleaning elements of the gizzard are carried and supplied by the gasometric dome.

The body 2.1 of the gizzard constitutes for the main part the bearing of the mechanical stirrer 2.3 of the digestion compartment, rotated by the gasometric dome 4. Optionally, it is also the support of a fixed biomass zone, encapsulated in one or more filtering device(s) 2.4, allowing at the same time to accumulate active biomass useful for digestion and to ensure thorough post-processing of the effluent which has to pass through this zone before its discharge.

In a preferred varied embodiment, shown by FIG. 2, the fixed biomass area 2.4 is imprisoned in a cartridge forming an interchangeable and removable subassembly with the mechanical stirrer 2.3, the reason being that said subassembly constitutes a pre-inoculatable and potentially evolutive part in order to accelerate the start or the restart of the digester, that can thus take advantage of the permanent development of the biomass supports (size, form, structured and/or nanostructured surface states of the materials of the filling elements) and that, in certain specific cases, the dynamic cooperation of the stirrer can be conceived in order to guarantee or improve operation of the fixed biomass, for example to mechanically counteract the tendency to auto-clog.

Said cartridge 3.21 of fixed biomass is connected to the double-walled piping 1.15 of the distribution unit via the opening 1.16, so that the cleaned liquid effluent which comes out of it converges parallel to the liquid fraction coming from the phase separator 2.2, towards the same flow and level regulation device 6.12, housed in the compartment 6.1 of holder 6.

The distribution and circulation unit 3 is a subassembly composed of the compartmentalized housing 3.1 connected to the circuits of circulating substrates and waste, in which the volumetric pump 3.3 as well as a distributor 3.2 are housed, here with four ways and four positions, itself controlled by an indexer 3.4 which, according to the considered constructive variants, may be inside or outside the circulation unit or the tank itself.

The core of the four-way distributor is preferably, also, in the form of a removable cartridge 3.21 able to be extracted with or separately of the pump and the indexer according to the circumstances mentioned. Said cartridge 3.21 includes the rotating shell, that can be spherical, its seats, useful bearings and gaskets. As the cartridge concentrates all the wearable parts of the mechanism, its simple replacement is equivalent to the total revision of the distributor.

Besides, the housing 3.1 of the circulation unit 3 is the seat and the support of several specific functions and/or accessories, among them a radial distribution device 3.6 for the supply loads in the digestion compartment of the tank 1, and a device 3.5 for recirculation of the biogas in its capacity as means for agitation of the fermentative environment, connected to the opening 1.17 of the double wall of piping 1.14.

In the present conception:
- the aperture or, as an alternative, the housing 3.31 of the pump, houses the bearing of its cardan shaft and fixes its stator 3.34. Both arrangements include a part in the form of a flange which constitutes the base of the gizzard and includes the substrate intake ports.
- Said part in the form of a flange includes means for rapid attachment of the subassembly formed around the pump and, in the case mentioned as an alternative, the connections of its motor.
- Once the gasometric dome 4 has been lowered and the active biomass zone thus insulated, the totality of the kinematic chain of the digester becomes accessible for maintenance, with the possibility to use the telescopic bracket 5.1 to extract the removable elements and if necessary, wash the inside of the gizzard under high pressure, with direct discharge of the residuals and washing water to the sewerage or into a suitable retention tank.

Operation of the Distributor the first indexing position P1 of the distributor 3.2 establishes the transfer circuit of the substrate between the grinder and the gizzard by the pipe 1.11 the second indexing position P2 of the distributor 3.2 establishes the homogenization circuit of the substrate by recirculation within itself via the opening 1.12 of the distributor 3.2 leading to the openings 2.13 of the double wall of gizzard 2, the third indexing position P3 of the distributor 3.2 establishes, via duct 1.13 that supplies chamber 3.13 for mixing and distribution of the substrate in the digestion compartment, from the gizzard. The same indexing position also allows, by exploiting mainly the direction of rotation of the pump and the relative levels of the digestion compartment and of the gizzard, to establish homogenization circuits for the fermentative environment by recirculation on itself, with overflowing of the fermentative environment from the gizzard and the possibility to correct the dryness thereof, with the help of the phase separator 2.2.

in operation, the fourth indexing position P4 of the distributor establishes, by the pipe 1.14, in one direction, a circuit of dosed introduction of co-substrate(s) from the container 8.2 in the gizzard and, in the other direction, a circuit for temporarily storing waste momentarily crushed in excess in the buffer tank 8.1. It also allows to supply a second digestion tank working as a slave to the first.

in maintenance, the position P3 of the distributor allows to occasionally purge the contents of the gizzard to the outside of the machine, for example in case of an accumulation of non-degradable residuals in the latter.

The gasometric dome 4 is composed of two parts, 4.1 and 4.2, dividing the dome in two concentric and annular volumes by a cylindrical wall connected to the part 4.1, of the same diameter as the overflow of the phase separator 2.2 which surmounts the gizzard, so that when said dome is no longer lifted by the pressure of the gas, it falls down and insulates the gizzard from the digestion compartment by applying fluid-tightly on the joint 2.23 which extends on the circumference of the phase separator 2.2.

The external compartment 4.1 of the dome includes a hydraulic joint 4.11 on its periphery, which allows its gas-tight movement in height and in rotation. Said compartment also includes the female part 4.12 of the jaw clutch 5.31 driving the dome by mobile equipment 5.3 of the bracket 5, on the one hand and, on the other, the female part 4.13 of the driving sheath of the stirrer 2.3 of the digestion compartment.

The gasometric dome is centred by the mobile equipment 5.3 which drives it, as well as by the stirrer 2.3 and, if necessary, by three equidistant shoes or rollers guided by the wall of the hydraulic joint 4.11.

The central compartment 4.2 of the dome is arranged as a removable gate which includes in its centre, in one of the constructive versions at least, the hydraulic joint 4.21, allowing the passage and the gas-tight rotation of the driving axle 3.32 of the volumetric pump 3.3 situated at the bottom of the gizzard 2.

Thus:
- the fluid-tightness of the gasometric dome towards the outside is ensured by one or two hydraulic gaskets 4.11 and 4.21, the protection levels of which are regulated to guarantee this fluid-tightness at the operating pressure of the biogas,
- in case of accidental deviation of pressure in the bioreactor, the gasometric dome also has the function of a security valve.
- by way of its rotation, the gasometric dome also drives the mechanical stirrer 2.3 of the digestion compartment, ensuring at the same time permanent sweeping of the area of the floating materials,
- by its vertical displacement, the dome allows in a very simple way to provide a continuous indication of the production and the consumption of biogas.

The hydraulic block 5, articulated around the pivoting telescopic bracket 5.1, is at the same time the central power supply and the support of the whole kinematic linkage of the internal elements of the digester. In the variant shown here, the unique electric motor is immersed in an oil container of the hydraulic group 5.2, respectively for its silence and for the recovery of its operation heat, for heating the digester. Located inside the thermostated and insulated enclosure of the machine, the hydraulic unit is protected against outside weather conditions.

According to constructive variants, it can be attached to or integrated in the tank, or fastened to the holder 6.

The kinematic chain of the digester is actuated from the top of the latter:
- the telescopic part of the bracket is formed by the shaft of a hydraulic jack 5.11 integrated into the hydraulic group 5.2,
- the bracket 5.1 is fixed at the end of this shaft and carries, according to the considered constructive variant, only one or two concentric drive rings 5.41 and 5.42, respectively of the driving axle of the pump, at the centre and, outside, of the driving jaw clutch 5.31 of the gasometric dome, which for its part drives the mechanical stirrer of the digestion compartment, symmetrically by the same means.

in low operation position, the bracket and its mobile equipment guide the rotation of the pump and the gasometric dome, in both directions and at the desired speeds. Furthermore, it includes the means and the captors necessary for the conjoint measuring of the parameters of use and security, such as speeds and direction of rotation in relation with the reactive couples opposed by the environment worked in.

in the upper maintenance position, the bracket is disconnected and releases the gate 4.2, for access to the central compartment of the gasometric dome.

Besides, it can carry pressurised cleaning tools for the gizzard, and/or tools for extracting the removable elements accessible by the latter.

Moreover, in case of substantial maintenance, which necessites unconfining or voiding the digestion area of the machine, it can lift, pivot, and set down the gasometric dome 4 as well as all the internal elements of the digester on any support, for example a maintenance carriage.

The holder 6 carries all the external elements of the digester which are not directly connected to the tank and confines the others. It is formed with fluid-tight or not fluid-tight compartments, arranged around the gasometric dome to form a bodywork which is weatherproof and/or protected against any unauthorized intervention. According to the execution variants of the machine and its working conditions, the holder will carry different bodyworks, of which only one example is represented here.

The holder 6 is a zone of the digester that is adaptive to its environment and to its working conditions. It is a structurally independent subassembly, which can be used for all the tank variants.

The compartment 6.1 manages the retention conditions of the biogas produced and its treatment through to the consumption counter. For this purpose it houses:

a water buffer container 6.11, with centralized device for maintaining the level of the liquid traps of the gasometric dome at their target value, as well as for regulation 6.12, of adjustable water trap systems for extracting the liquid effluents coming from the phase separator 2.2 and the fixed biomass cartridge 2.31, the outlet of which will depend on its local valorization possibilities.

a hydrogen sulphide filter, water separator, useful captors and other circuit functions collected in a ventilated sub-compartment 6.13.

security means adapted to the installation conditions of the digester.

The same compartment additionally concentrates, in the variant of FIG. 2, all the connections of the digester to its environment, by a preinstalled underground technical duct with its base 1.5, which furthermore collects and evacuates run-off water, excess process water and washing water coming from maintenance.

The compartment 6.2 manages the use and/or the exportation of biogas, from the consumption counter. For this purpose it houses:

a device for self-consumption of biogas by the digester, comprising the consumption counter, a boiler, a circulator and a valve or thermostatic cartridge of its heating circuit, a device for derivation of heat and/or of excess biogas towards a consumer outside the digester, (valorization)

a security and alarm device which directs the biogas towards an appropriate outlet that is without danger in case of breakdown of the boiler, mini flare or other, elements for ventilation of the compartment and discharge of the burnt gas, as well as appropriate security detectors, in particular for its internal temperature.

The compartment 6.3 houses the hydraulic group 5.2 which ensures the production, the distribution and the differentiated regulation of hydraulic energy respectively used for motorization of the distribution and circulation unit 3, rotation of the gasometric dome 4, operation of the telescopic bracket 5.1 and pressurizing of the supply water of the cleaning and self-cleaning devices of the machine.

The heat dissipated by its operation is recovered for heating the digester.

The compartment 6.4 contains the whole electric part of the digester in two different boxes:

a high current electrical box, 6.41 houses the terminal connector of the digester for connection to the electricity network, fuses and the start-up relay for the hydraulic group, circulators and other single or three-phase peripherals.

a low current electrical box, 6.42 connecting the programmable controller to all its peripherals for measuring, control and remote transmission, an operation control interface with alphanumeric display, alarms and computer connection means for maintenance.

Constructive Variant

In this constructive variant, (FIG. 2), which is justified by the possibility to be free of the tank's geometry and/or by the need to carry out maintenance in its lower part, in particular when the lower part can be advantageously sunk in the ground, said tank is made with the totality of its connections attached to its upper part and, in the variant proposed here, made in two easily separable parts in order to be able to perform, if needed, a fast exchange of the upper part without having to void the contents of the tank.

In this case:

reheating the incoming matter is no longer associated to the lower part 1.2 of the tank itself, but to its upper part 1.1 forming a cover.

The distribution and circulation unit 3 is still carried by its supply pipes but the latter are now connected to the cover part 1.1 of the tank, The bottom of the lower part 1.2 of the tank 1 remains conical or inclined to concentrate sediments, and their purge is done through the emptying opening 1.18, by gravity or by pumping according to execution variants and the type of installation.

Below a certain size of the digester, the part forming a cover of the tank will be easily removable and can be set down in one unit with minimal perturbation for the fermentative environment, by trained operators and according to a process respecting all security conditions.

It will be also possible to replace the whole digester with the same ease, and, if appropriate, to replace a machine already in operation, for example by means of a truck equipped with a crane, like the example of a standard container lifter equipped with a crane.

Second Embodiment

Figure 6:
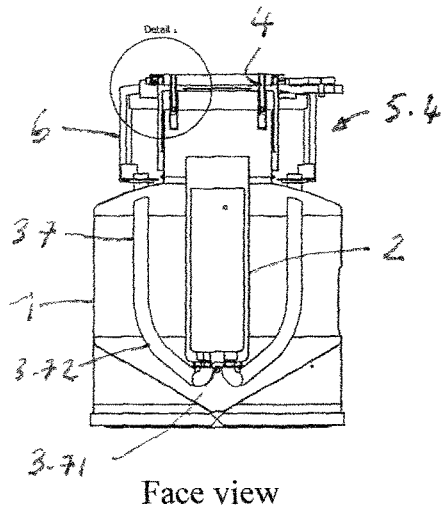
FIG. 6: includes several views of a second embodiment.
Figure 6:
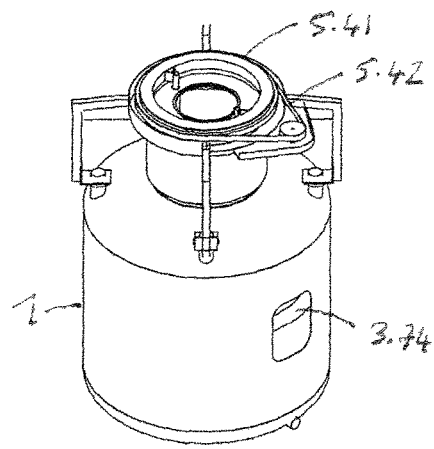
Figure 6:
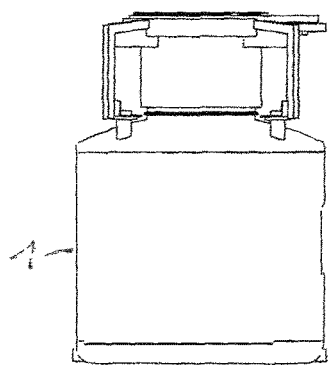
Figure 6:
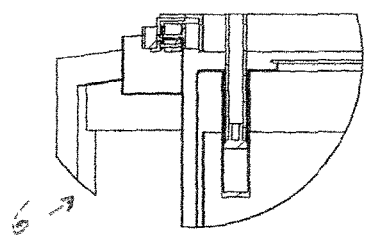
Figure 6:
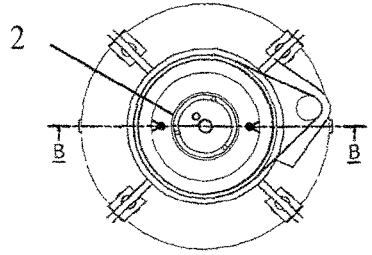
Figure 6:
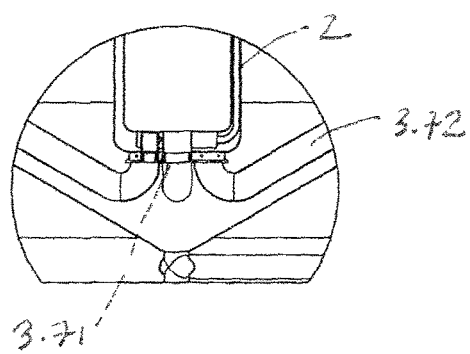

FIG. 6 describes an embodiment which represents a variant of the rotating drive device of the gasometric dome 4 and its integration with the holder 6 part of the digester, to jointly form a constructive subassembly which is distinct and removable as such, like the gizzard 2.

Figure 7:
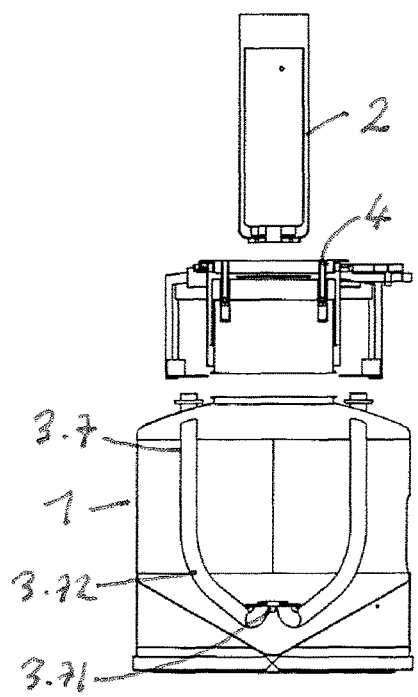
FIG. 7: includes three supplementary views of the second embodiment.
Figure 7:
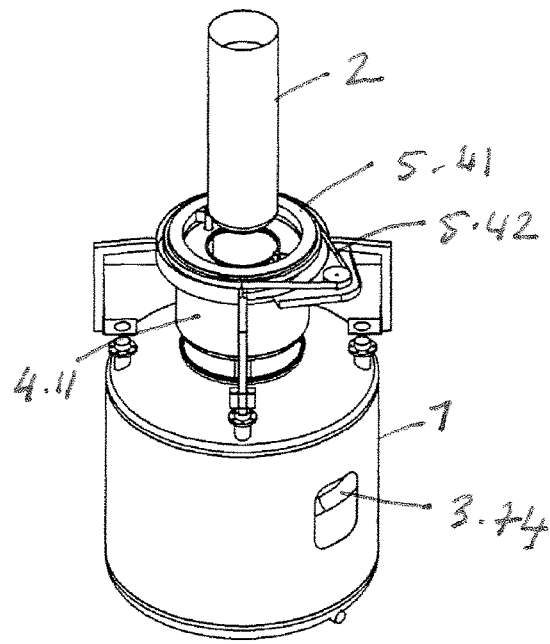
Figure 7:
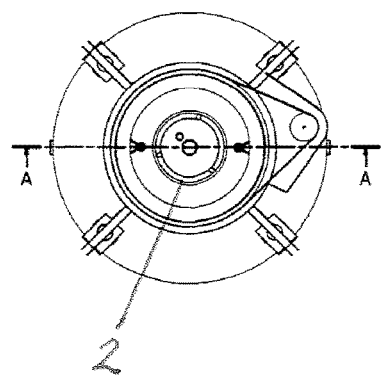

FIG. 7 shows this original partition of the digester in three different functional subassemblies and its general conception in its capacity as machine intended for being mass produced in industrial quantities. This is different from the container-contained embodiments of currently found installations.

In the present embodiment, what one can call the removable head 5.4 of the digester rests on the end of pipes 3.72 constitutive of the upper part of a cradle 3.7 of the gizzard 2 which at the same time constitutes a mechanically transport element and a transition between the external and confined spaces of the machine.

Unlike the variant shown by FIG. 2, where the tank has a cover bolted along a peripheral joint arranged on its circumference, the present embodiment dissociates the fastening of the parts that can be separated from their sealing area.

Here, the mechanical function of maintaining fluid-tightness is provided by the points of support and fastening of the head 5.4 of the digester, formed by the integration of its hydraulic joint and holder parts.

As represented in FIGS. 6 and 7, the driving device of the digester's mobile equipment is constituted by a crown 5.41 associated with a pulley 5.42 the rolling path of which follows the top of the hydraulic joint located on the outside.

In this constructive variant, dispensing with the bracket is achieved with attendant accessibility to the internal elements of the machine, through the gate 4.2 of the gasometric dome to access the inside of the gizzard 2, or, after dismounting the driving crown 5.41, or access the tank 1 itself after extraction of the gizzard 2.

The gizzard 2 is connected to its cradle and thus to the rest of the machine by simple plugging into the plate 3.71 of its cradle, where it is fixed, here by screws accessible from the inside of its central compartment, once the hydrasive grate is withdrawn.

The different compartments of the gizzard 2 are connected individually to the external elements of the digester by ducts forming its cradle 3.74, like the stirring device of the main compartment of the tank 1 (by recirculation of the biogas) and the useful captors and probes.

The plate of the cradle also connects the central compartment of the gizzard 2 to an outlet allowing its direct emptying or by an internal device (not represented)—arranged between the cradle and the base of the tank—or external, for separating unwanted not degradable matter and recycling the liquid part in the digester.

These connections are provided in the axis of the tank 1 in case of available space under the latter or if not perpendicularly, by concentric pipes, respectively connected to the tank 1 (external pipe) and to the gizzard 2 (internal pipe).

Peripherals

This invention aims to offer, for the first time, a real alternative to the use of dustbins and to their drawbacks in the places of transformation of foodstuffs or food.

The condition for reaching this is to supply to the operating staff the means to get rid of organic wastes immediately, as they are produced, as easily as throwing them into the dustbin, but without the nuisances.

This means has been found by the intelligent connection of the digester to one or more hygienic grinding units that are extremely low-noise and automatized and that integrate directly in work stations or in their immediate proximity.

The waste grinding unit 7 thus constitutes the entry point of the materials to be treated and is ideally located in the places of waste production.

From a certain quantity to be treated, one finds grinders which do the job well enough, generally used in systems where waste is collected and crushed in the liquid phase, then transported by piping to the location of dustbins where they will be wringed-dry, the liquid fraction returning it to a closed waste transport circuit where the pulped part, neutralized with a bactericide to avoid its spontaneous composting inside said dustbins, is eliminated by refuse collection.

For lower quantities to be treated, there is a range of domestic waste disposal units, generally forbidden by law because of the large organic load that they dump in the sewerages and their high consumption in drinking water.

In the present invention, following a specific approach to biomethanisation, the quantity of water allocated to the process is determined according to the desired dryness of the substrate at the entry of the digester, with for consequence the need to manage consumption from the grinding level onwards.

This specific approach, including the grinding step in the total accounting of water needs, creates a permanent and supplementary functional link between the digester and its grinder(s), independently of the distance which separates them.

For restaurants whose size is taken as example to illustrate the invention, this approach not only leads to the already mentioned advantage to be able to relocate the digester in relation to the waste production place, but also to the possibility to directly integrate the grinding elements in the given work surface(s) so that the passage of waste in any dustbin is unnecessary and immediately perceived as such.

For satisfying these conditions while respecting those of perfect hygiene and safety, the grinding blocks are endowed with self automatization means for certain functions, for example security or self-cleaning, but which are controlled by the controller of the digester for those which could interfere with its operation, for example the dilution of incoming matter.

We hereinafter describe two variants 7a and 7b of these grinding units, both conceived to fit in a work surface, the first in the context of a restaurant, opening by a tilt door like an oven or a dish-washer, the second in an industrial environment, where chain-working conditions impose uninterrupted managing of the waste.

It stands to reason that the described principle can be applied to a wide range of situations and that many variants can be extrapolated without exceeding the scope of this invention.

FIG. 4 is a schematic representation of the grinding unit 7a in its working position, where it can be seen that the tilting part 7.1 is composed of the door panel which includes useful controls 7.2 like electronic control unit 7.21, hopper 7.3 and grinder 7.4.

In this particular case, the tilt door 7.1 drives the hopper 7.3, at the bottom of which the opening of the grinder 7.5 is positioned, providing a tilt allowing total emptying of the hopper inside the grinder at the end of a grinding cycle.

The grinder used here is a proven product of the market, sometimes called disintegrator because of its operating principle which associates a stator in the form of a peripherally-toothed crown to a rotor which is also toothed, whose cooperation with the stator combines the grinding effect with that of a pump, which sucks the waste against the upstream grinding area and conveys its residuals in a downstream discharge piping.

Generally conceived to work online, the grinder is used here in a different way to prepare substrate loads in a closed circuit with the hopper via the piping 7.6 which links it to the outlet 7.7.

These loads are then pumped in one go in the gizzard 2 of the digester, according to an automatized cycle which restores the hopper of the crushing block, empty and rinsed, via nozzles 7.81 disposed in a compartment 7.8 which covers the latter during the crushing cycle and sucks its emanations when it is opened, by an opening 7.82.

To ensure this containment function of projections of matter generated during the crushing and washing stage of the hopper by means of the mentioned nozzles, as well as aspiration of the emanations, in the present embodiment the compartment 7.8 is fixed on its frame 7.7 by a pin 7.83 which allows it a slight range of movement, controlled by an actuator 7.13 also anchored on the frame 7.7, which also anchors the actuation device 7.14 of the door of the grinding unit, in this case to jack(s).

By this means, the compartment rises by some mm at the moment of the unlocking of the door 7.1, which spares the joint 7.31 of the hopper 7.3 at the moment of opening on the one hand, and on the other hand creates the space necessary for a slight aspiration of the surrounding air, for carrying away the emanations of the hopper if it contains waste. According to the operation place of the apparatus, this function will be ensured by a specific device of the grinding block or by connection to the general ventilation of the building. When the grinding cycle is asked for, the same device applies the compartment on the hopper when locking the door and thus ensures that the cycle follows its course in total containment. The compartment 7.8 also contains pressurizing elements 7.84 and reheating elements 7.85 for the washing water of the hopper.

In the present embodiment, the subassembly formed by the hopper 7.3 and of the grinder 7.4 is articulated on two coaxial side branches 7.61 and 7.62 of the piping 7.6, mounted therethrough on two bearings 7.63 connected to a frame 7.7 suspended and sliding on rails 7.91 carried by the frame 7.9 of the piece of furniture which houses and bodies the grinding unit itself.

The ends of pipes 7.61 and 7.62 are connected fluid-tightly and rotatably with two valves 7.71 and 7.72, secured to the frame 7.7, respectively connected in a pluggable way with two pipes 7.92 and 7.93, one leading to the digester and the other to the sewerage. The latter pipes are equipped with stopcocks 7.94 and 7.95, carried by the frame 7.9, that can be closed from the front of the grinder.

In case of maintenance, the removable subassembly overall formed by the hopper 7.3, grinder 7.4, frame 7.7 and compartment 7.8 can be first insulated, unlocked, and withdrawn from its housing, to undergo an intervention on the spot or to be replaced, in a few minutes.

A drawer 7.96 placed under the pluggable device allows to properly recover the liquid fraction which flows out necessarily at the moment of the disconnection of the pipes.

In most cases, unwanted objects are the cause of grinder breakdowns in the domain of catering; generally cutlery.

If this happens, the object, which is generally jammed in the mouth of the grinder under the pile of waste, is not accessible after emptying the hopper.

In the present conception, to simplify this type of operation, if it happens at the beginning of the processes, where the waste is still in a solid or pasty state, a gate 7.11 has been provided in the door 7.1, exactly facing the mouth of the grinder, in order to be able to access the unwanted object, or even unlock the rotor of said grinder without emptying the hopper totally.

In normal operation, the door of the device can indifferently remain opened or closed and its hopper can contain waste temporarily, the emanations of which will be aspirated.

Movements of the door of the grinding unit are assisted by its actuation device, so that the operator only needs to command its opening or closure, by different means (button, pedals, proximity detector, voice . . . ) which constitute many options. The door of the grinding unit as well as its gate are provided with locking devices 7.12 which authorize the start of a cycle only after having been activated.

The grinding unit works under the control of the digester's controller which in certain circumstances can, according to the installed peripheral options, forbid its use or deviate the flow of crushed waste towards a permanent or temporary buffer container 8.1. An indicator light signals a disturbance.

Operation of the Peripheral Device

To access to its functions, the door 7.1 of the grinding unit has to be closed and its gate 7.11 correctly in place. When discharge of the waste is asked for, the door and its gate lock by means of electric actuators 7.12 at the same time as the compartment 7.8 is applied on the joint 7.31 of hopper 7.3.

A small quantity of water is dosed by certain nozzles to trigger the grinder and the latter is activated for a programmed duration. The waste is aspired from the hopper 7.3 into the grinder 7.4 to return in closed circuit by the pipes 7.6, until forming a homogeneous "soup" that can be pumped easily.

Then, the valve 7.71 of the circuit for transferring crushed matter towards the digester opens, allowing the pump of the latter to aspire and account for the contents of the hopper, until deactivation of the grinder. At this moment, a second quantity of boiling water is injected under low flow but high pressure by the nozzles 7.81, in the grinder's hopper, in order to wash it. This water is then again aspirated in the piping leading to the digester, so that it also cleans it during its passage.

Then the valve 7.71 closes again and the grinding unit is ready for use.

At appropriate intervals, disinfection cycles inputting a detergent are intercalated between the supply cycles of the digester. When they have been programmed to operate sequentially, the automatic lock of the door of the conditioning unit is prolonged accordingly, the chosen disinfection cycle starts, with the difference compared to the supply of the digester that the discharge will be done on this occasion towards the sewerage, by the valve 7.72.

Variant and Constructive Extension

The described example of grinding unit 7a shows the capacity of integration of the invention in the environment of a restaurant kitchen, comparable to a fryer, i.e. by taking at most the place of a small dustbin.

In the industrial agrifood environment, which imposes almost permanent operating conditions to this kind of equipment, the present conception also finds its place in a preparation chain.

To illustrate this, FIG. 5 represents a setup 7b associating two subassemblies composed of a grinder, its hopper, and the compartment which surmounts it, the implementation of which is alternated in order to be able to supply the digester without interrupting the workflow on the one hand and, on the other hand, where the disinfection process of the work surfaces can be combined with that of the grinders.

In this variant, the door 7.1 of the first variant is replaced by a safety and cleanliness frame 8.1, which ensures locking of the system in each of its work positions by being applied on the joint of the hopper which receives the waste. In so doing so it prevents waste from infiltrating the frame 8.2.

Optionally, said frame 8.1 can have a security device which forbids swinging movement of the two adjoining hoppers 8.3, each equipped with their grinder 8.4, under the effect of its actuation device 8.5.

Apart from that, the principle of operation remains the same, as before there are compartments 7.8, pipes 7.6, 7.92, 7.93, valves 7.71 and 7.72 of the transfer circuit for ground matter towards the digester and washing waters towards the sewerage, respectively, and also stopcocks 7.94 and 7.95, and all the usual devices and components common to the two facilities, mentioned or not, such as electrical and electronic connection and control units.

It stands to reason that the grinders/peripherals described referring to FIGS. 3 to 5 can be advantageously used with the apparatus of FIG. 1 or 2; however they can also be used with other types of apparatus for receiving and treating organic waste by anaerobic bioconversion including a closed tank.

General Process

At the digester, the substrate introduced into the gizzard is first stirred on itself by the pump and the blade of its mechanical stirrer. Then, with the pump running, the distributor is positioned for a supply sequence of the digestion compartment from the gizzard where the dosage is measured by the number of revolutions of the pump. Then the distributor repositions in gizzard stirring mode.

The supply of the digestion compartment has raised the level in the latter and caused overflowing of the substrate over the overflow of the phase separator, which will filter the supernatant liquid fraction and redirect the non digested materials into the gizzard, where they will mix with the materials during stirring.

The internal stirring of the gizzard is then interrupted to leave place to a stirring sequence of the digestion compartment by its stirrer, both to share the supply charge in the whole fermentative environment and to homogenize the contents, followed by a rest time until the next cycle.

From cycle to cycle, hour after hour, the gizzard is emptied to leave place for new waste coming from the grinder(s) installed at the production places.

According to the composition of the substrate, more or less frequent purges will be necessary for avoiding a heavy residual sedimentation at the bottom of the tank and the very improbable accumulation of unwanted light matter, which tend to accumulate in the area of the floating matter. If called for, their elimination will be caused by overflowing the floating matter in the gizzard and consecutive emptying of the latter by the position P3 of the distributor.

The invention claimed is:

1. An apparatus for receiving and treating organic waste by anaerobic bioconversion comprising a closed tank (1) which constitutes a bioconversion site, provided in an upper part of the closed tank with a device (4) for storing and pressurizing biogas produced, the closed tank (1) comprising a main enclosure that surrounds an internal and central secondary enclosure which the internal and secondary enclosure is surmounted by a liquid-solid phase separator (2.2), characterized in that:
    the internal and central secondary enclosure is a gizzard (2) comprising a cylindrical gizzard body mounted removably along a central axis of the closed tank (1), the cylindrical gizzard body (2) constituting a rotational bearing coupled to a rotatable mechanical stirrer (2.3),
    the gizzard (2) forms a sub-assembly with, or is removably connected to, a circulation and distribution unit (3) arranged to control flux of substrate inside the closed tank (1) of the apparatus,
    said device (4) for storing and pressurizing biogas produced is a gasometric dome (4) mounted for axial displacement and configured to rotate with the rotatable mechanical stirrer (2.3), driven in rotation by a motorisation device (5.41,5.42) that does not interfere with the axial displacement of the gasometric dome (4), the rotatable mechanical stirrer (2.3) being arranged and configured to agitate a fermentative environment contained in the main enclosure of the closed tank (1), and
    the gasometric dome (4) is configured to be retractable or at least partly retractable to provide access to internal parts of the apparatus and to allow the gizzard (2) to be removed from the apparatus.

2. The apparatus according to claim 1, characterized in that the gasometric dome (4) has two concentric compartments (4.1,4.2), of which a first compartment (4.1) is outside and surmounts the main enclosure of the closed tank (1) and which a second compartment (4.2) is located centrally of the gasometric dome (4) and surmounts the gizzard (2), in such a way that, in case of a depressurization of the apparatus, the gasometric dome (4) fits on a gasket (2.23) arranged on a circumference of the phase separator (2.2) which surmounts the gizzard (2) and fluid-tightly insulates the phase separator (2.2) and the gizzard (2) from the main enclosure of the closed tank (1).

3. The apparatus according to claim 2, characterized in that an upper part of said second compartment (4.2) located centrally of the gasometric dome is formed by a gate which gives access to inside the gizzard (2) with neither rupturing containment of the main enclosure of the closed tank (1) nor perturbing anaerobic biological processes occurring in the main enclosure of the closed tank (1).

4. The apparatus according to claim 1, characterized in that the distribution and circulation unit (3) has a compartmentalized housing (3.1) connected to circuits for circulating substrate, in which compartmentalized housing (3.1) a volumetric pump (3.3) is housed as well as a multi-way distributor (3.2) controlled by an indexer (3.4).

5. The apparatus according to claim 1, characterized in that:
    the closed tank (1) is made of a single part and carries external elements of the apparatus on an attached holder (6).

6. The apparatus according to claim 1, wherein the apparatus is connected to one or more peripherals each including a grinder (7a,7b) ensuring particle reduction to materials introduced in the gizzard (2).

7. The apparatus according to claim 6, characterized in that the apparatus comprises:
    a programmable controller arranged for ensuring accounting of flow of materials and fluids circulated inside the apparatus or exchanged by the latter with its environment, as well as surveillance and regulation of parameters that might interfere with its operation of the programmable controller;

said accounting includes counting of the water consumption of each of the grinders ($7a,7b$) connected to the apparatus in relation with the waste quantities respectively introduced by the latter, in order to control the dilution rate.

8. The apparatus according to claim 1, wherein said sub-assembly formed by the gizzard (2) and the circulation and distribution unit (3) situated at a base of the gizzard (2) forms both a support and the rotational bearing of the rotatable mechanical stirrer (2.3) for the fermentative environment contained in the main enclosure of the tank (1).

9. The apparatus according to claim 1, wherein the gizzard (2), which constitutes a support and rotational bearing coupled to the rotatable mechanical stirrer (2.3), is connected to the circulation and distribution unit (3) located inside of the closed tank (1) and carried by a holder (6).

10. The apparatus according to claim 1, wherein the motorization device (5.41, 5.42) of the gasometric dome (4) is carried by an arm (5.1) of a telescopic bracket located at the top of the apparatus, or the motorization device comprises a driving crown (5.41).

11. The apparatus according to claim 1, wherein the closed tank (1) is made of two separable parts, a lower part which can be fixed in the ground, and an upper part formed by a cover equipped with a holder (6), which upper part is detachable.

* * * * *